US010568695B2

(12) United States Patent
Codella et al.

(10) Patent No.: US 10,568,695 B2
(45) Date of Patent: Feb. 25, 2020

(54) SURGICAL SKIN LESION REMOVAL

(71) Applicant: International Business Machines Corporation, Armonk, NY (US)

(72) Inventors: Noel C. Codella, White Plains, NY (US); Jonathan H. Connell, Cortlandt-Manor, NY (US); Sharathchandra Pankanti, Darien, CT (US); Nalini K. Ratha, White Plains, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/275,877

(22) Filed: Sep. 26, 2016

(65) Prior Publication Data

US 2018/0085166 A1 Mar. 29, 2018

(51) Int. Cl.
*A61B 5/00* (2006.01)
*A61B 34/10* (2016.01)
*H04L 29/08* (2006.01)
*G06T 7/00* (2017.01)
*A61B 17/3205* (2006.01)
*A61B 17/00* (2006.01)

(52) U.S. Cl.
CPC ............ *A61B 34/10* (2016.02); *G06T 7/0012* (2013.01); *H04L 67/10* (2013.01); *A61B 17/3205* (2013.01); *A61B 2017/00761* (2013.01); *A61B 2034/107* (2016.02); *G06T 2207/30088* (2013.01); *G06T 2207/30096* (2013.01)

(58) Field of Classification Search
CPC .......... C07K 2317/24; C07K 2317/565; A61B 5/0064; A61B 5/0075; A61B 5/0077
USPC ......... 600/300, 587, 595; 356/370; 359/385, 359/386
See application file for complete search history.

(56) References Cited

U.S. PATENT DOCUMENTS 3,769,963 A * 11/1973 Goldman ................ A61F 9/008
219/121.63
5,381,224 A * 1/1995 Dixon ................ G01N 21/6456
250/458.1
5,719,700 A * 2/1998 Corcuff ................ A61B 5/0068
359/211.5

(Continued)

FOREIGN PATENT DOCUMENTS

EP 2172147 A1 4/2010

OTHER PUBLICATIONS

Codella et al., "Deep Learning, Sparse Coding, and SVM for Melanoma Recognition in Dermoscopy Images," Springer International Publishing Switzerland; pp. 1-9, 2015.

(Continued)

*Primary Examiner* — May A Abouelela
(74) *Attorney, Agent, or Firm* — Cantor Colburn LLP; Anthony Curro

(57) ABSTRACT

Embodiments include methods, systems, and computer program products for treating skin lesions. Aspects include receiving an indication that a patient is oriented. Aspects also include acquiring data concerning an area of the patient, the area including a skin lesion. Aspects also include analyzing the data to distinguish between an affected region and an unaffected region of the area of the patient. Aspects also include excising the affected area.

4 Claims, 7 Drawing Sheets

(56) References Cited

U.S. PATENT DOCUMENTS

| | | | | |
|---|---|---|---|---|
| 5,760,950 A * | 6/1998 | Maly | G02B 21/0028 | 359/368 |
| 5,788,639 A * | 8/1998 | Zavislan | A61B 5/0059 | 600/473 |
| 5,880,880 A * | 3/1999 | Anderson | G02B 21/0036 | 359/368 |
| 6,032,071 A * | 2/2000 | Binder | A61B 5/0059 | 356/369 |
| 6,424,852 B1 * | 7/2002 | Zavislan | A61B 5/0068 | 600/407 |
| 6,462,345 B1 * | 10/2002 | Simon | G02B 21/0056 | 250/458.1 |
| 6,745,067 B1 * | 6/2004 | Zavislan | A61B 5/0066 | 600/473 |
| 7,004,902 B2 * | 2/2006 | Luce | A61B 3/1005 | 600/398 |
| 7,047,064 B1 * | 5/2006 | Zavislan | A61B 5/0059 | 359/368 |
| 7,139,122 B1 * | 11/2006 | Eastman | A61K 49/001 | 359/386 |
| 7,938,821 B2 * | 5/2011 | Chan | A61B 18/203 | 606/10 |
| 8,045,263 B2 | 10/2011 | Yaroslavsky et al. | | |
| 8,140,141 B2 * | 3/2012 | McGreevy | A61B 5/0059 | 600/300 |
| 8,224,427 B2 * | 7/2012 | Kopriva | A61B 5/0059 | 600/476 |
| 8,562,546 B2 * | 10/2013 | Shih | A61B 5/0053 | 310/321 |
| 8,911,988 B2 * | 12/2014 | Miller | A61B 5/1405 | 435/288.7 |
| 8,971,609 B2 | 3/2015 | Gareau et al. | | |
| 9,195,043 B2 * | 11/2015 | Ghosh | G02B 21/16 | |
| 9,254,174 B2 * | 2/2016 | Lukac | A61B 18/203 | |
| 2003/0009110 A1 * | 1/2003 | Tu | A61B 5/053 | 600/547 |
| 2004/0133112 A1 * | 7/2004 | Rajadhyaksha | A61B 5/0059 | 600/476 |
| 2005/0046936 A1 * | 3/2005 | Dixon | G02B 21/0024 | 359/385 |
| 2006/0132790 A1 * | 6/2006 | Gutin | A61B 5/0066 | 356/479 |
| 2006/0268402 A1 * | 11/2006 | Eustergerling | A61B 5/0059 | 359/386 |
| 2007/0249913 A1 * | 10/2007 | Freeman | A61B 5/0059 | 600/300 |
| 2008/0024860 A1 * | 1/2008 | Yaroslavsky | A61B 5/0068 | 359/372 |
| 2008/0049990 A1 * | 2/2008 | Melchi | A61B 5/0059 | 382/128 |
| 2008/0226151 A1 * | 9/2008 | Zouridakis | A61B 5/0059 | 382/133 |
| 2009/0218527 A1 * | 9/2009 | French | G02B 21/004 | 250/578.1 |
| 2009/0318815 A1 * | 12/2009 | Barnes | A61B 5/742 | 600/473 |
| 2010/0081928 A1 * | 4/2010 | Hyde | A61B 5/0084 | 600/431 |
| 2010/0082019 A1 | 4/2010 | Neev | | |
| 2010/0168586 A1 * | 7/2010 | Hillman | G02B 23/2476 | 600/476 |
| 2010/0292543 A1 * | 11/2010 | Levitt | G01N 21/6456 | 600/300 |
| 2011/0116694 A1 * | 5/2011 | Gareau | G01N 21/6458 | 382/128 |
| 2011/0137144 A1 * | 6/2011 | Rofougaran | H04L 12/6418 | 600/407 |
| 2011/0172565 A1 * | 7/2011 | Shih | A61B 5/0053 | 600/587 |
| 2012/0170037 A1 * | 7/2012 | Yaroslavsky | A61B 5/0059 | 356/370 |
| 2012/0170828 A1 * | 7/2012 | Gareau | G06K 9/00147 | 382/133 |
| 2012/0220878 A1 * | 8/2012 | Sullivan | A61B 5/0059 | 600/476 |
| 2013/0079599 A1 * | 3/2013 | Holmes | G06F 19/366 | 600/300 |
| 2013/0338447 A1 * | 12/2013 | Gilad-Gilor | A61B 5/0077 | 600/300 |
| 2014/0030799 A1 * | 1/2014 | Yu | G01N 15/1056 | 435/287.2 |
| 2014/0213909 A1 * | 7/2014 | Mestha | A61B 5/0077 | 600/476 |
| 2015/0374309 A1 * | 12/2015 | Farkas | G01N 21/21 | 600/473 |
| 2015/0374451 A1 | 12/2015 | Kim | | |
| 2016/0018632 A1 | 1/2016 | Gareau | | |
| 2016/0022193 A1 * | 1/2016 | Rau | A61B 5/165 | 600/301 |
| 2016/0124202 A1 | 5/2016 | Huang et al. | | |
| 2017/0231550 A1 * | 8/2017 | Do | G06T 7/11 | 382/128 |
| 2017/0329929 A1 * | 11/2017 | Fishman | A61B 5/0077 | |

OTHER PUBLICATIONS

Gutman et al., "Skin Lesion Analysis Toward Melanoma Detection: A Challenge at the Internationial Symposium on Biomedical Imaging" (ISBI) May 2016, hosted by the International Skin Imaging Collaboration (ISIC), six pages.

* cited by examiner

SURGICAL SKIN LESION REMOVAL

BACKGROUND

The present invention relates to removal of cancerous skin lesions, and more specifically, to automated methods and apparatus for removal of cancerous skin lesions.

When a skin lesion, such as a skin melanoma, is diagnosed as cancerous patients can undergo surgical procedures to have the affected tissue removed. To prevent or minimize recurrence and renewed growth of a skin lesion, it is often necessary to remove all of the cancerous tissue. For instance, in a procedure referred to as Mohs Surgery, a clinician removes a portion of a skin lesion, and with interaction with a pathology laboratory, determines whether further tissue should be removed in a subsequent surgical excision, which generally occurs in the same day. Sometimes multiple iterations of surgical procedures can be needed to remove affected tissue in its entirety.

SUMMARY

In accordance with one or more embodiments, a computer-implemented method for treatment of skin lesions is provided. The method includes receiving, by a processor, an indication that a patient is oriented. The method also includes acquiring, by the processor, data concerning an area of the patient, the area including a skin lesion. The method also includes analyzing, by the processor, the data to distinguish between an affected region and an unaffected region of the area of the patient. The method also includes providing an output signaling a need for interaction.

In accordance with another embodiment, a computer program product for treatment of skin lesions is provided. The computer program product includes a non-transitory storage medium readable by a processing circuit and storing instructions for execution by the processing circuit for performing a method including receiving an indication that a patient is oriented. The method also includes acquiring data concerning an area of the patient, the area including a skin lesion. The method also includes analyzing the data to distinguish between an affected region and an unaffected region of the area of the patient. The method also includes providing an output signaling a need for interaction.

In accordance with a further embodiment, a processing system for treating skin lesions includes a processor in communication with one or more types of memory. The processor is configured to receive an indication that a patient is oriented. The processor is also configured to acquire data concerning an area of the patient, the area including a skin lesion. The processor is also configured to analyze the data to distinguish between an affected region and an unaffected region of the area of the patient. The processor is also configured to provide an output signaling a need for interaction.

BRIEF DESCRIPTION OF THE DRAWINGS

The subject matter of the present invention is particularly pointed out and distinctly claimed in the claims at the conclusion of the specification. The foregoing and other features and advantages of the one or more embodiments described herein are apparent from the following detailed description taken in conjunction with the accompanying drawings in which:

DETAILED DESCRIPTION

Figure 1:
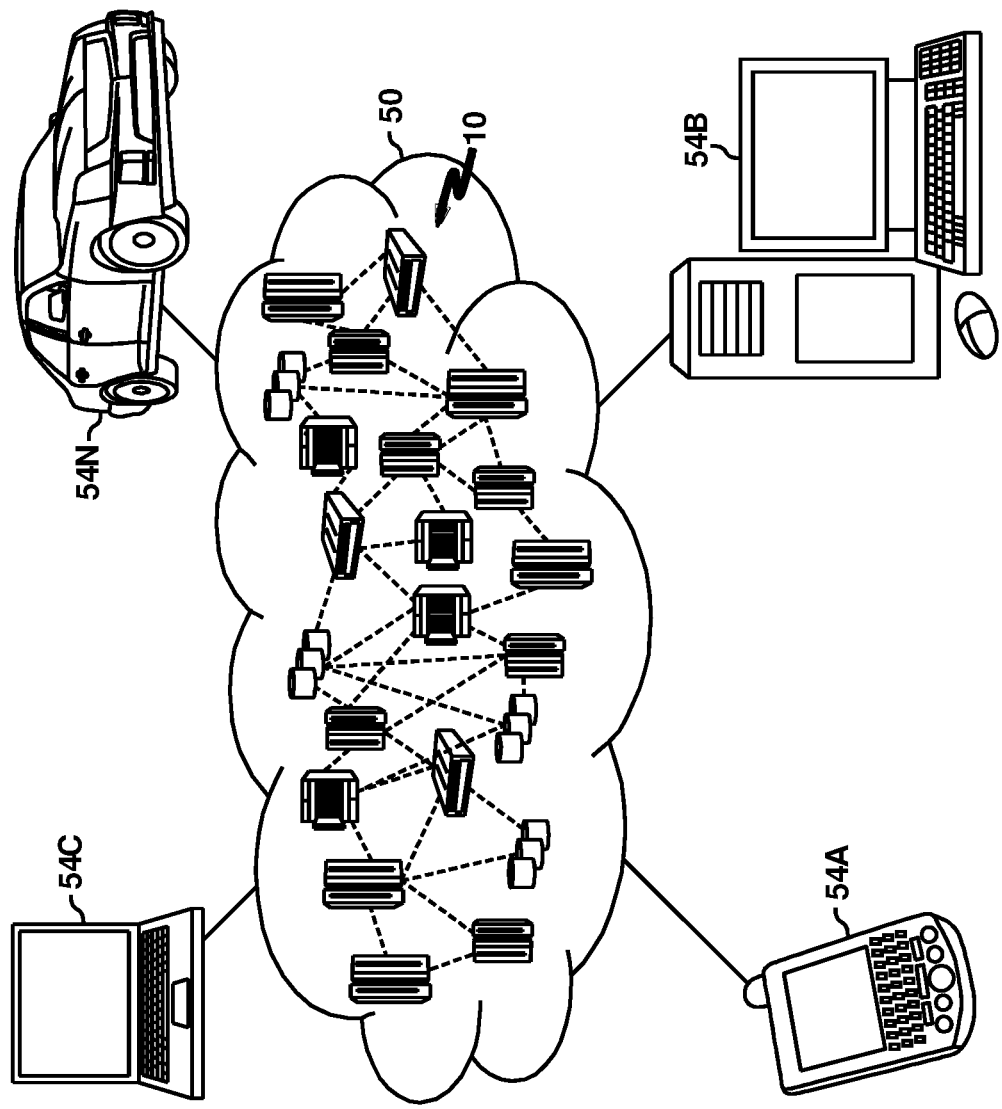
FIG. 1 depicts a cloud computing environment according to an embodiment of the present invention.

Systems and methodologies for removal of cancerous skin lesions are provided. Conventionally, when a skin lesion has been diagnosed as cancerous, patients can undergo a procedure called "Mohs Surgery." In Mohs Surgery, a dermatologist or other healthcare clinician can remove some tissue containing the lesion and send the tissue to a pathology lab. The patient, conventionally, waits with an open wound while a report is generated and returned to the clinician that details if and where any cancerous tissue remains. The clinician, after receiving the report can then return to the patient to remove more tissue, send newly excised tissue to the pathology lab, and repeat the remainder of the process. In some cases, several iterations could be conducted before all cancerous tissue is removed. Mohs surgery can thus be highly time consuming, costly, and uncomfortable for patients undergoing the procedure.

Embodiments described herein include automated systems and methods for detection of cancerous tissue, surgical planning, and surgical execution. Methods and systems described herein can reduce the time and cost for removing cancerous skin lesions and can increase the comfort level of the patient relative to conventional methods. Some embodiments provide display of affected areas of a skin lesion and interaction with a clinician including surgical action. In some embodiments, detecting cancerous tissues in real-time and providing automated, computer implemented analysis of tissues can reduce the risk of complications, reduce expenses, and increase patient comfort.

It is understood in advance that although this description includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model can include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but can be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It can be managed by the organization or a third party and can exist on-premises or off-premises.

Community cloud: the cloud infrastructure is shared by several organizations and supports a specific community that has shared concerns (e.g., mission, security requirements, policy, and compliance considerations). It can be managed by the organizations or a third party and can exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure including a network of interconnected nodes.

Referring now to FIG. 1, illustrative cloud computing environment 50 according to one or more embodiments of the present invention is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N can communicate. Nodes 10 can communicate with one another. They can be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
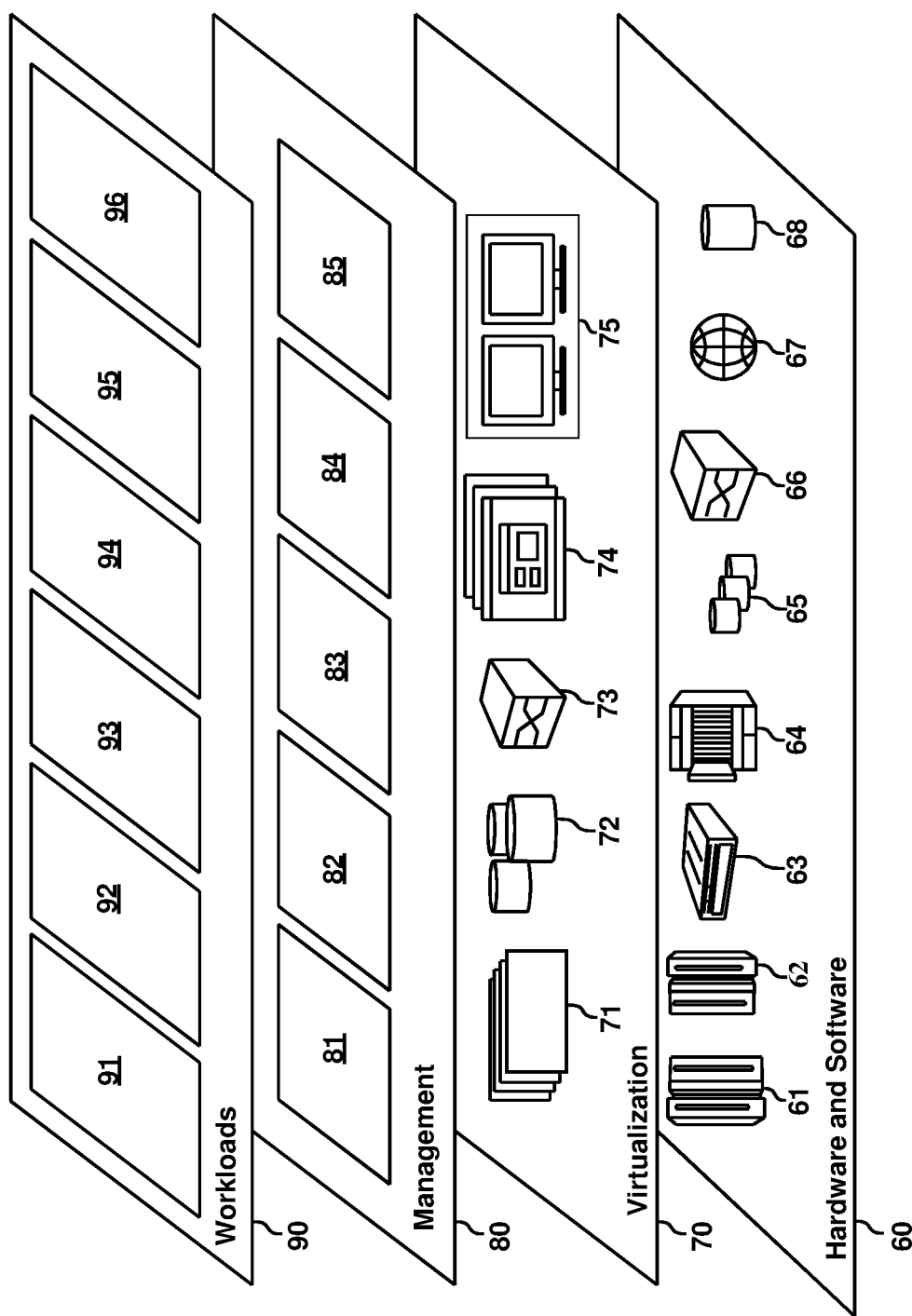
FIG. 2 depicts abstraction model layers according to an embodiment of the present invention.

Referring now to FIG. 2, a set of functional abstraction layers provided by cloud computing environment 50 (FIG. 1) according to one or more embodiments of the present invention is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities can be provided: virtual servers 71; virtual storage 72; virtual networks 73, including virtual private networks; virtual applications and operating systems 74; and virtual clients 75.

In one example, management layer 80 can provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources can include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment can be utilized. Examples of workloads and functions which can be provided from this layer include: mapping and navigation 91; software development and lifecycle management 92; virtual classroom education delivery 93; data analytics processing 94; transaction processing 95; and analysis of images of skin lesions to distinguish between affected and unaffected regions 96.

Figure 3:
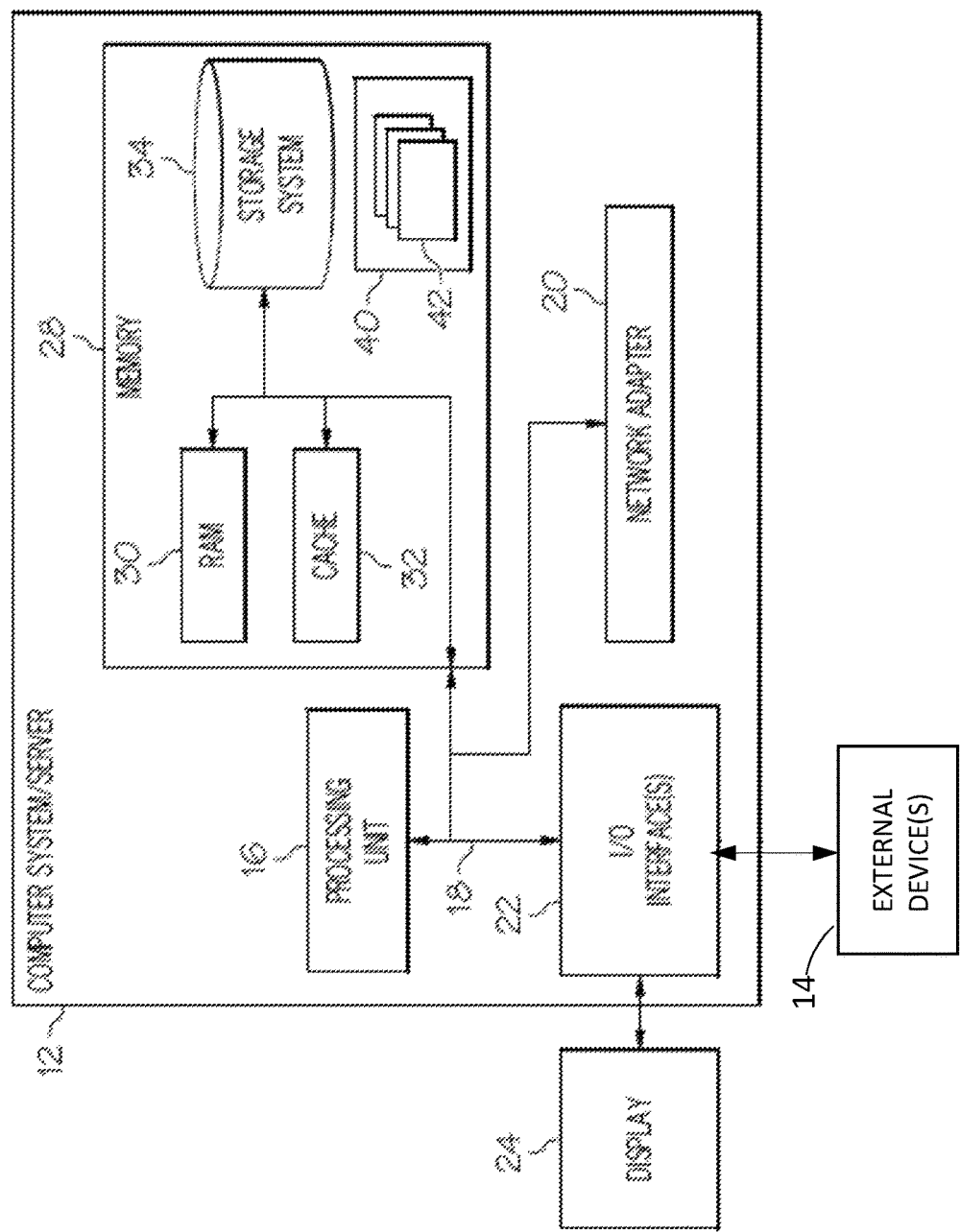
FIG. 3 depicts a computer system according to one or more embodiments of the present invention.

Referring now to FIG. 3, a schematic of a cloud computing node 100 included in a distributed cloud environment or cloud service network is shown according to one or more embodiments of the present invention. The cloud computing node 100 is only one example of a suitable cloud computing node and is not intended to suggest any limitation as to the scope of use or functionality of embodiments of the invention described herein. Regardless, cloud computing node 100 is capable of being implemented and/or performing any of the functionality set forth hereinabove.

In cloud computing node 100 there is a computer system/server 12, which is operational with numerous other general purpose or special purpose computing system environments or configurations. Examples of well-known computing systems, environments, and/or configurations that can be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 can be described in the general context of computer system-executable instructions, such as program modules, being executed by a computer system. Generally, program modules can include routines, programs, objects, components, logic, data structures, and so on that perform particular tasks or implement particular abstract data types. Computer system/server 12 can be practiced in distributed cloud computing environments where tasks are performed by remote processing devices that are linked through a communications network. In a distributed cloud computing environment, program modules can be located in both local and remote computer system storage media including memory storage devices.

As shown in FIG. 3, computer system/server 12 in cloud computing node 100 is shown in the form of a general-purpose computing device. The components of computer system/server 12 can include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media can be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 can further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 can include at least one program product having a set (e.g., at least one) of program modules that are configured to carry out the functions of embodiments of the invention.

Program/utility 40, having a set (at least one) of program modules 42, can be stored in memory 28 by way of example, and not limitation, as well as an operating system, one or more application programs, other program modules, and program data. Each of the operating system, one or more application programs, other program modules, and program data or some combination thereof, can include an implementation of a networking environment. Program modules 42 generally carry out one or more functions and/or methodologies in accordance with some embodiments of the present invention.

Computer system/server 12 can also communicate with one or more external devices 14 such as a keyboard, a pointing device, a display 24, etc., one or more devices that enable a user to interact with computer system/server 12, and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Embodiments of the present invention provide automated real-time feedback to a surgeon or clinical team obviating the need to wait for results from a separate pathology lab. Embodiments of the present invention perform robust analysis on tissue that remains attached to a patient. In some embodiments, the equivalent of cellular level pathology can be performed on tissue attached to a patient.

Figure 4:
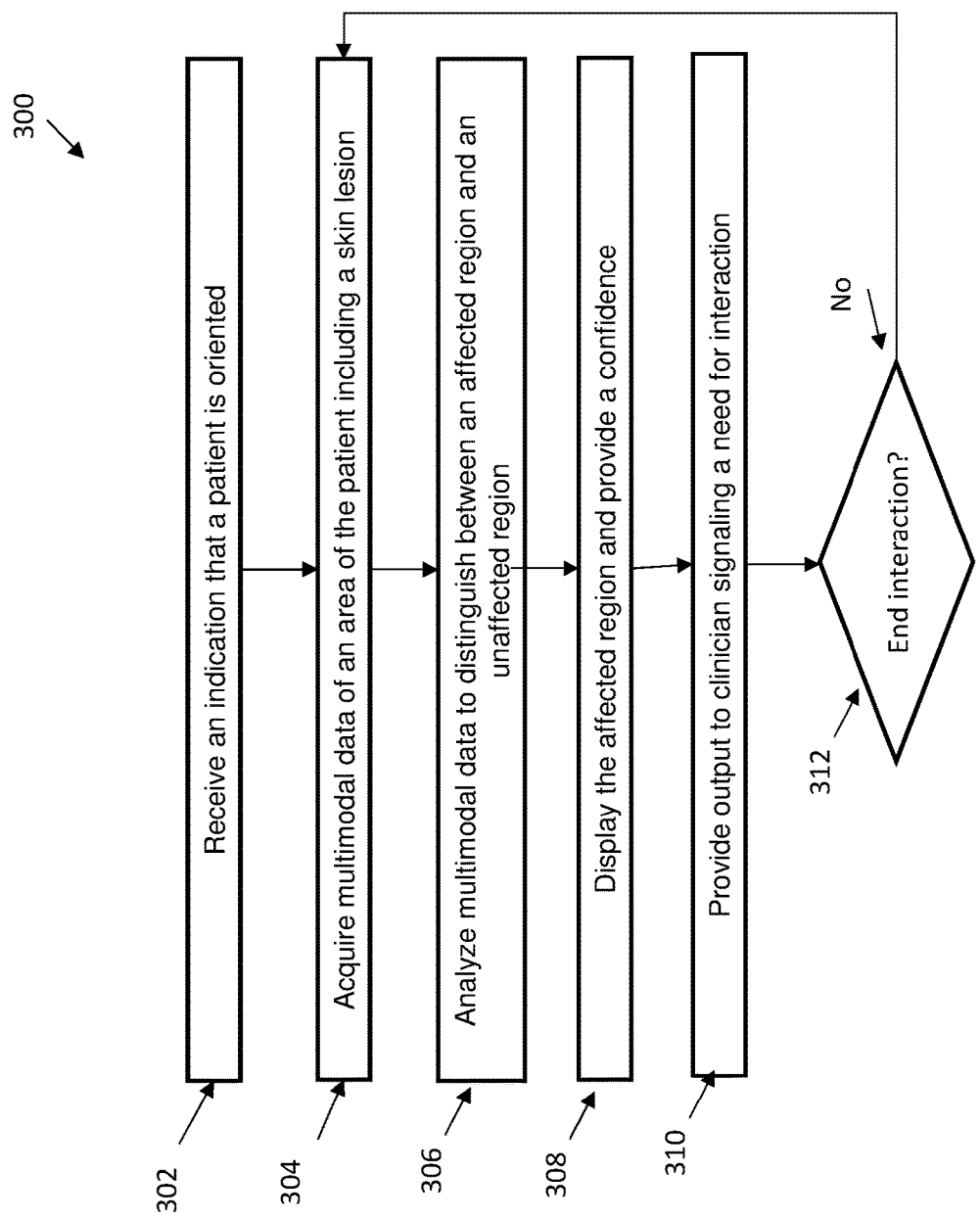
FIG. 4 is a flow diagram illustrating a method for treatment of skin lesions according to one or more embodiments of the present invention.

Referring now to FIG. 4, a flow chart illustrating an exemplary method 300 for treatment of skin lesions according to one or more embodiments of the present invention is shown. According to the method 300, an indication that a patient is oriented with respect to a visual data acquisition apparatus is received, as shown at block 302. For example, when a patient is oriented, a clinician can provide an input to a system indicating the patient is oriented. In some embodiments, the indication that a patient is oriented includes supplying power to a system. The exemplary method 300 also includes acquiring multimodal data of an area of the patient including a skin lesion, as shown at block 304. Then, as is shown at block 306, the method 300 includes analyzing the multimodal data to distinguish between an affected region and an unaffected region. The exemplary method 300 also includes displaying the affected region and providing a confidence level for a calculated boundary, as shown at block 308. The confidence level for the calculated boundary can be provided visually, audibly or textually. The exemplary method 300 includes providing an output to a clinician signaling a need for interaction. For example, the output to the clinician signaling a need for interaction can include providing a visual, audible, or textual cue that an analysis is complete and an affected area is identified and ready for removal. In some embodiments, the method 300 optionally includes determining whether to end the interaction, as shown at decision block 312. Responsive to a determination not to end the interaction, the method can return to block 304. For example, after a clinician or surgical team excises an affected region or a portion of an affected region, the clinician or team can desire to reassess whether affected areas remain present. Thus, after surgical intervention, the method 300 can again acquire multimodal data and continue. After a signal is received to end the interaction, the data acquisition and other method steps can stop. In some embodiments, a clinician can repeat the process until it is determined that no affected areas remain present.

In some embodiments, the method 300 optionally includes determining whether the affected region was completely removed from the area of the patient and, responsive to a determination that the affected region was not completely removed, providing a second boundary data output. In some embodiments, the second boundary data output includes calculated boundaries of a remaining affected region. In some embodiments, the method 300 also optionally includes providing a second output to the clinician signaling a second need for interaction.

In some embodiments, the method 300 includes excising the affected region or a portion of the affected region. In some embodiments, the method 300 includes excising all of the affected region. The affected region can be removed by any known method and can be performed manually, for example by a clinician, or automatically, for example in a computer-assisted or machine-assisted manner or without clinician interaction. The affected region can be removed, for instance, mechanically such as with a scalpel, with a laser, or with cryogenic freezing.

In some embodiments, the method 300 includes receiving user feedback. For example, the user feedback can include clinician modifications to an affected region boundary or to the calculated confidence.

Multimodal data can include a plurality of data types pertaining to the patient's condition. In some embodiments, the multimodal data includes confocal microscopy data. In some embodiments, the multimodal data includes dermoscopy data. In some embodiments, the multimodal data includes optical coherence tomography (OCT) data. The multimodal data can include real-time data, static data, or a combination thereof. The multimodal data includes data that can assist a clinician in determining the presence and location of affected regions of a skin lesion. Affected regions include regions of a patient containing cancerous or pre-cancerous skin cells.

Analyzing the multimodal data includes automated analysis of multiple data sources to determine the presence or absence of affected regions. Methods of analyzing the multimodal data to distinguish between an affected region and an unaffected region are known and any such methods can be used in accordance with the method 300 for treatment of skin lesions. For example, analyzing the multimodal data can include conducting a pixel-by-pixel analysis of a digital image of a skin lesion to eliminate noise and artifacts and running, for instance, a classifier algorithm using color and histogram data. For example, luminance of a pixel, intensity, hue, and saturation values can be assigned to each pixel and compared to neighboring pixels. Based upon the comparison, in some embodiments, a calculated boundary for an affected area can be calculated. In some embodiments, the confidence level for the calculated boundary can also be calculated.

Displaying the affected region includes providing a visual output to a clinician to demonstrate a spatial representation of boundaries of an affected region. In some embodiments, the affected portion with or without an associated confidence is displayed by overlaying a light on an affected area of the patient. In some embodiments, the affected portion with or without an associated confidence is displayed by projecting an image of the patient on a separate display and highlighting the affected region on the display. In some embodiments, the affected portion is displayed by providing an output to feedback system, such as an automated system that robotically marks the affected region on the patient body with an ink source. In some embodiments, the affected portion is displayed to a clinician with a heads up display, including virtual reality glasses or augmented reality glasses.

In some embodiments, a confidence level for the calculated boundary, which can be associated with distinguishing the affected region from the unaffected region, is calculated. In some embodiments the confidence is communicated to a clinician on a display, such as a computer or tablet display. In some embodiments, the confidence is overlaid on an image of the patient's skin.

In some embodiments, the method 300 optionally includes implanting a therapeutic or cosmetic material into a treated area. The treated area includes a region in which an affected area had been removed. For example, the method can include filling the treated area with a biological glue, sutures, or cosmetic agents to mask or correct the appearance of missing biological tissue.

Figure 5:
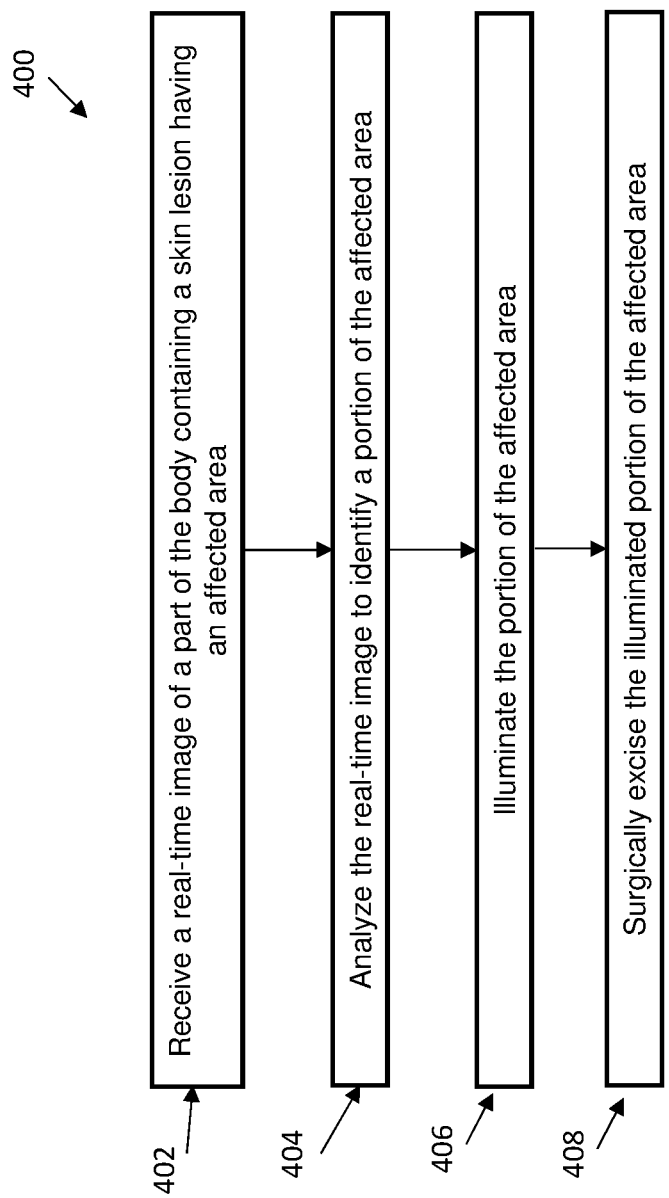
FIG. 5 is a flow diagram illustrating another method for treatment of skin lesions according to one or more embodiments of the present invention.

FIG. 5 is a flowchart of another exemplary method 400 for treatment of skin lesions according to one or more embodiments of the present invention. According to the method 400, a real-time image of a part of the body containing a skin lesion having an affected area is received, as shown at block 402. The method 400 also includes, as shown at block 404, analyzing the real-time image to identify a portion of the affected area. The method 400 also includes illuminating the portion of affected area, as shown at block 406. In some embodiments, the method 400 can also include surgically excising the illuminated portion of the affected area, as shown at block 408.

Figure 6:
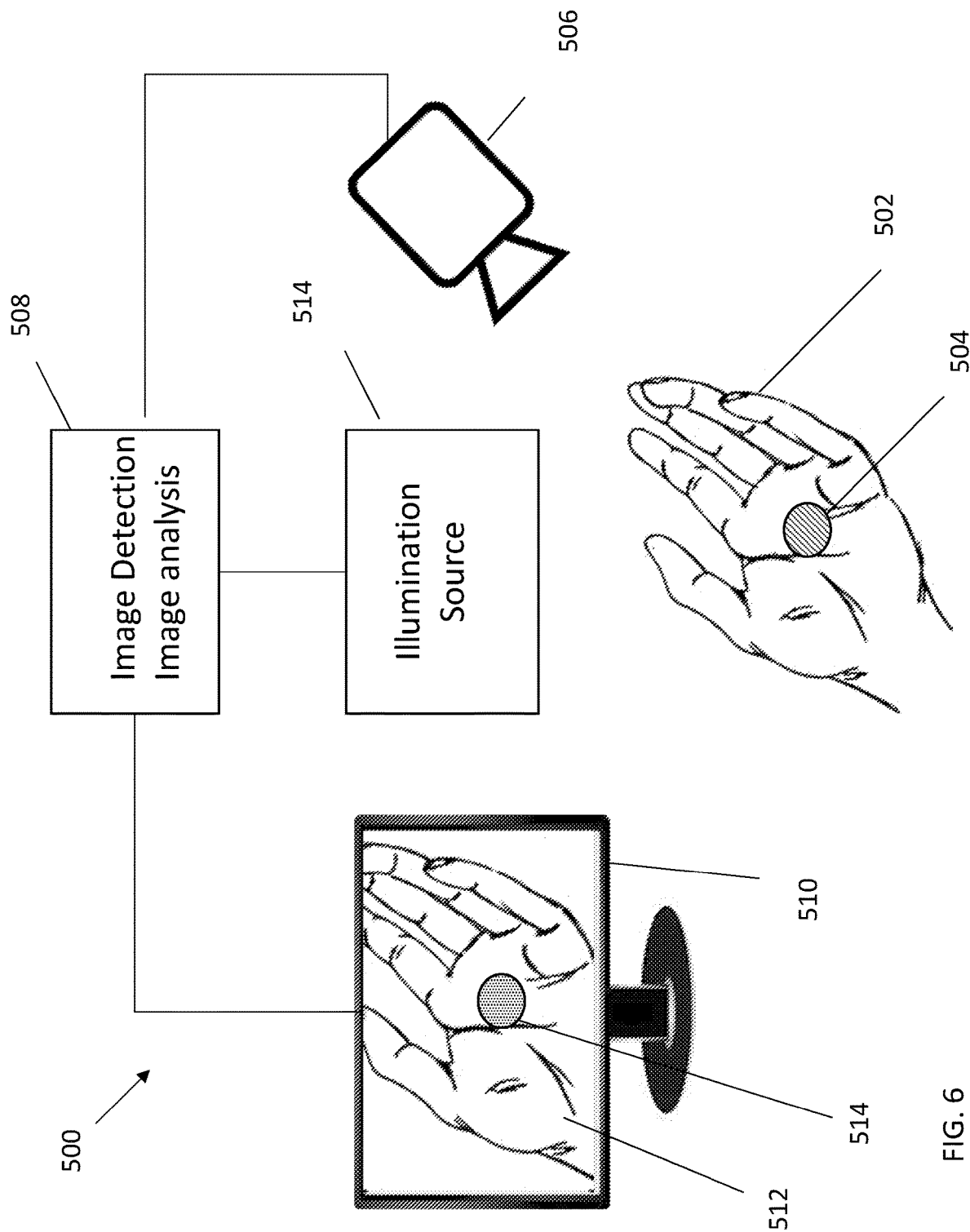
FIG. 6 depicts a diagram illustrating an exemplary system for treatment of skin lesions according to one or more embodiments of the present invention.

FIG. 6 illustrates an exemplary system 500 for treatment of skin lesions according to one or more embodiments of the present invention. A patient 502 having a skin lesion 504 can be oriented in proximity to a visual data acquisition apparatus 506. The visual data acquisition apparatus 506 can include, for example, a camera such as a camera suitable for clinical photography, a microscope such as a confocal microscope, a dermascope, or an OCT apparatus. The visual data acquisition apparatus can be connected to an image detection and analysis system 508. The image detection and analysis system can include a single component or can include a plurality of components. The system 500 can also include a display 510. The display 510 can depict an image of the patient 512. The image of the patient 512 can include an image of the affected region and surrounding unaffected region. The display 510 can include a visualization of the affected region 514. The visualization of the affected region 514 can include all or part of the affected region of a skin lesion. The visualization of the affected region 514 includes an output of the image analysis from the image detection and analysis system 508.

Figure 7:
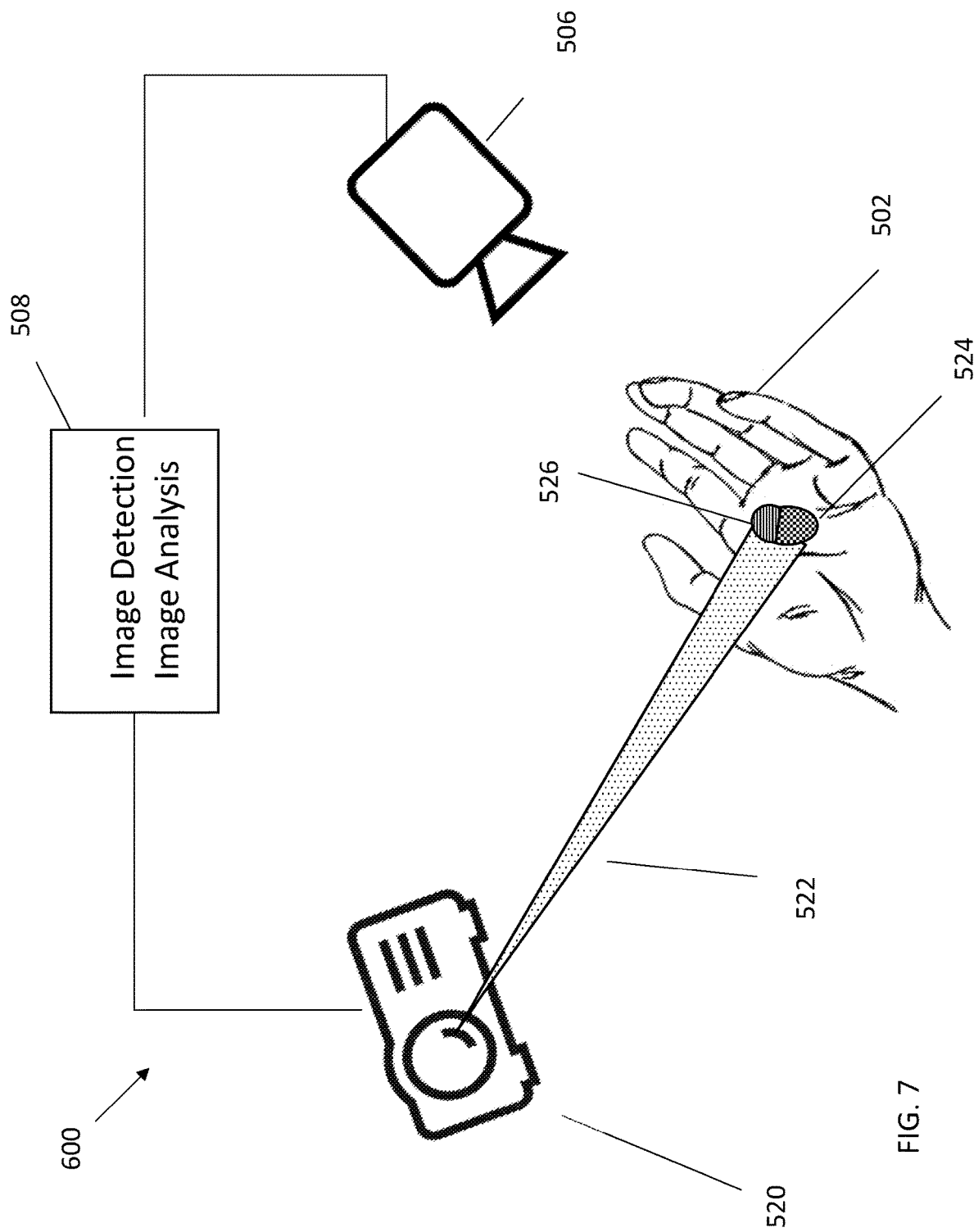
FIG. 7 depicts a diagram illustrating another exemplary system for treatment of skin lesions according to one or more embodiments of the present invention.

FIG. 7 illustrates another exemplary system 600 for treatment of skin lesions according to one or more embodiments of the present invention. A patient 502 can be oriented in proximity to a visual data acquisition apparatus 506. The visual data acquisition apparatus can be connected to an image detection and analysis system 508. The image detection and analysis system can provide an output to a projector 520, which can provide a visual output 522. The visual output 522 can include a light that distinguishes between an affected region 524 and an unaffected region 526.

In some embodiments, systems 500, 600 optionally include a therapeutic or cosmetic agent delivery device. The therapeutic or cosmetic agent delivery device can be capable of delivery or implanting therapeutic or cosmetic agents into the treated area.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form described. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The flow diagrams depicted herein are just one example. There can be many variations to this diagram or the steps (or operations) described therein without departing from the spirit of embodiments of the invention. For instance, the steps can be performed in a differing order or steps can be added, deleted or modified. All of these variations are considered a part of the claimed invention.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method for treatment of skin lesions, the method comprising:
    acquiring, by a processor, multimodal data comprising digital images concerning an area of a patient, the area comprising a skin lesion, wherein the multimodal data comprises one or more of confocal microscopy data, dermoscopy data, or optical coherence tomography data;
    analyzing, by the processor, the multimodal data to distinguish between an affected region and an unaffected region of the area of the patient;
    determining, by the processor, a boundary of the affected region;
    projecting, by a projector, an image onto a surface of a patient's skin, the image comprising a visual indication that distinguishes between the affected region and the unaffected region, the visual indication including the boundary;
    automatically, by a mechanical process, excising the affected region based upon the analysis, wherein the mechanical process is controlled by a computer or machine without clinician interaction, and wherein excising the affected region defines an excised boundary;
    determining, by the processor, that the affected region was not completely removed from the area of the patient based on a multimodal analysis by the processor of tissue that remains attached to the patient, the tissue adjacent to the excised boundary; and
    responsive to the determination that the affected region was not completely removed, providing, by the processor, a second visual indication comprising a boundary of a remaining affected region.

2. The computer-implemented method of claim 1, wherein the affected region and the unaffected region are attached to the area of the patient.

3. A computer program product for treatment of skin lesions, the computer program product comprising:
    a computer readable storage medium readable by a processing circuit and storing program instructions for execution by the processing circuit for performing a method comprising:
    acquiring multimodal data comprising digital images concerning an area of the patient, the area comprising a skin lesion, wherein the multimodal data comprises one or more of confocal microscopy data, dermoscopy data, or optical coherence tomography data;
    analyzing the multimodal data to distinguish between an affected region and an unaffected region of the area of the patient;
    determining a boundary of the affected region;
    causing a projector to project an image onto a surface of a patient's skin, the image comprising a visual indication that distinguishes between the affected region and the unaffected region, the visual indication including the boundary;

automatically, by a mechanical process, excising the affected region based upon the analysis, wherein the mechanical process is controlled by a computer or machine without clinician interaction, and wherein excising the affected region defines an excised boundary;

determining that the affected region was not completely removed from the area of the patient based on a multimodal analysis of tissue that remains attached to the patient, the tissue adjacent to the excised boundary; and responsive to the determination that the affected region was not completely removed, providing a second visual indication comprising a boundary of a remaining affected region.

4. The computer program product of claim 3, wherein a software is provided as a service in a cloud environment.

* * * * *